United States Patent
Maruyama

(10) Patent No.: US 8,142,349 B2
(45) Date of Patent: Mar. 27, 2012

(54) ROTATION MECHANISM FOR ENDOSCOPE

(75) Inventor: Yoshinori Maruyama, Saitama (JP)

(73) Assignee: Hoya Corporation, Tokyo (JP)

( * ) Notice: Subject to any disclaimer, the term of this patent is extended or adjusted under 35 U.S.C. 154(b) by 956 days.

(21) Appl. No.: 12/137,755

(22) Filed: Jun. 12, 2008

(65) Prior Publication Data

US 2008/0319263 A1 Dec. 25, 2008

(30) Foreign Application Priority Data

Jun. 22, 2007 (JP) .................................. 2007-164779

(51) Int. Cl.
*A61B 1/00* (2006.01)
(52) U.S. Cl. .......................... 600/146; 600/147; 600/148
(58) Field of Classification Search ........... 600/146–148
See application file for complete search history.

(56) References Cited

U.S. PATENT DOCUMENTS

| | | | | |
|---|---|---|---|---|
| 3,788,303 A * | 1/1974 | Hall | ............................. | 600/148 |
| 4,742,816 A * | 5/1988 | Suzuki et al. | ................. | 600/134 |
| 4,825,850 A * | 5/1989 | Opie et al. | .................... | 600/122 |
| 5,007,406 A * | 4/1991 | Takahashi et al. | ............ | 600/119 |
| 5,014,685 A * | 5/1991 | Takahashi | ..................... | 600/148 |
| 5,507,717 A | 4/1996 | Kura et al. | | |
| 5,575,755 A * | 11/1996 | Krauter et al. | ................ | 600/148 |
| 7,828,725 B2 * | 11/2010 | Maruyama | .................... | 600/148 |
| 7,871,219 B2 * | 1/2011 | Maruyama | .................... | 403/362 |
| 2005/0137453 A1 | 6/2005 | Ouchi et al. | | |
| 2005/0197532 A1 | 9/2005 | Sasaki et al. | | |
| 2006/0088303 A1 | 4/2006 | Ito | | |
| 2007/0010713 A1 | 1/2007 | Negishi | | |
| 2007/0255104 A1 | 11/2007 | Maruyama | | |
| 2008/0114377 A1 | 5/2008 | Shibata et al. | | |

FOREIGN PATENT DOCUMENTS

| | | |
|---|---|---|
| JP | 7-194519 | 8/1995 |
| JP | 9-98942 | 4/1997 |
| JP | 10-286220 | 10/1998 |
| JP | 11-47082 | 2/1999 |
| JP | 2003-135384 | 5/2003 |
| JP | 2007-313292 | 12/2007 |

OTHER PUBLICATIONS

English language Abstract of JP 7-194519; Aug. 1, 1995.
English language Abstract of JP 9-98942, Apr. 15, 1997.
English language Abstract of JP 10-286220, Oct. 27, 1998.
English language Abstract of JP 11-47082, Feb. 23, 1999.
English language Abstract of JP 2003-135384, May 13, 2003.
English language Abstract of JP 2007-313292, Dec. 6, 2007.
U.S. Appl. No. 12/137,770 to Maruyama, filed Jun. 12, 2008.
U.S. Appl. No. 12/137,739 to Maruyama, filed Jun. 12, 2008.

* cited by examiner

*Primary Examiner* — Matthew J Kasztejna
(74) *Attorney, Agent, or Firm* — Greenblum & Bernstein, P.L.C.

(57) ABSTRACT

A connection mechanism includes a rotatable member formed with a connection hole in which a shaft member is rotatably fitted. A thrust stopper is arranged at the distal end of the shaft member to prevent the rotatable member from being removed from the shaft member. The shaft member has an outer-screw at the distal end portion thereof, and the thrust stopper has an inner-screw opening extending along an axial direction of the thrust stopper. The outer-screw of the distal end portion of the shaft member engages with the inner-screw opening. The thrust stopper has a through opening formed with an inner-screw with which a fixing screw engages. The tip end of the fixing screw engages with the distal end of the shaft member to secure fixation between the thrust stopper and the shaft member.

5 Claims, 4 Drawing Sheets

ROTATION MECHANISM FOR ENDOSCOPE

BACKGROUND OF THE INVENTION

The following descriptions relate to a rotation mechanism for an endoscope.

Generally, at an operation section of an endoscope, rotation mechanisms such as a mechanism for operating a bending portion of an insertion section of the endoscope, a mechanism for changing a rising angle of a treatment tool and the like are provided. Such a mechanism is configured such that an operating member (i.e., a rotating member) is rotatably supported by a shaft member, and a thrust stopper for preventing the operating member from being removed from the shaft member is provided at the distal end portion of the shaft member. Examples of such a structure are disclosed in Japanese Patent Provisional Publications No. 2003-135384 (hereinafter, referred to as '384 publication) and No. HEI 11-47082 (hereinafter, referred to as '082 publication).

Specifically, according to '384 publication, the thrust stopper contacting an distal end surface of the shaft member is secured thereto with a screw. According to '082 publication, a C-ring or an E-ring is engaged in a groove formed, at the distal end portion, on the circumferential surface of the shaft member. In either case, the position, in the axial direction of the shaft member, of the thrust stopper is fixed due to the structure of the shaft member.

At the distal end portion of the shaft member, which is remote from the proximal end that is secured to a frame of the operation unit of the endoscope, there may exist a dimensional error greater than expected tolerance since accumulated errors exhibit at the distal end portion. In such a case, the position of the thrust stopper with respect to the rotational member varies, and the rotational member may have a play in the axial direction (i.e., thrust direction) or the position of the thrust stopper is closer to the proximal end so that the rotational member does not rotate smoothly as the stopper urges the rotational member against the shaft member.

SUMMARY OF THE INVENTION

The present invention is advantageous in that an improved rotation mechanism which enables a smooth rotation of the rotation member regardless of the accumulated dimensional errors in the axial direction of the shaft member.

According to an aspect of the invention, there is provided a connection mechanism, which is provided with a shaft member, a rotatable member formed with a connection hole in which the shaft member is rotatably fitted at a distal end portion of the shaft member, a thrust stopper arranged at the distal end of the shaft member to prevent the rotatable member from being removed from the shaft member. The shaft member has an outer-screw at the distal end portion thereof, the thrust stopper having an inner-screw opening extending along an axial direction of the thrust stopper, and the outer-screw of the distal end portion of the shaft member engages with the inner-screw opening. The thrust stopper is provided with a through opening formed with an inner-screw and a fixing screw configured to engage with the inner-screw of the through opening. The fixing screw inserted in the through opening and engaged with the inner-screw engages with the distal end portion of shaft member to secure fixation between the thrust stopper and the shaft member.

With the above configuration, the thrust stopper is securely fixed to the distal end of the shaft member, a smooth rotation of the rotation member is enabled regardless of the accumulated dimensional errors in the axial direction of the shaft member.

BRIEF DESCRIPTION OF THE ACCOMPANYING DRAWINGS

DETAILED DESCRIPTION OF THE EMBODIMENTS

Hereinafter, referring to the accompanying drawings, connection mechanisms according to embodiments of the invention will be described.

Figure 2:
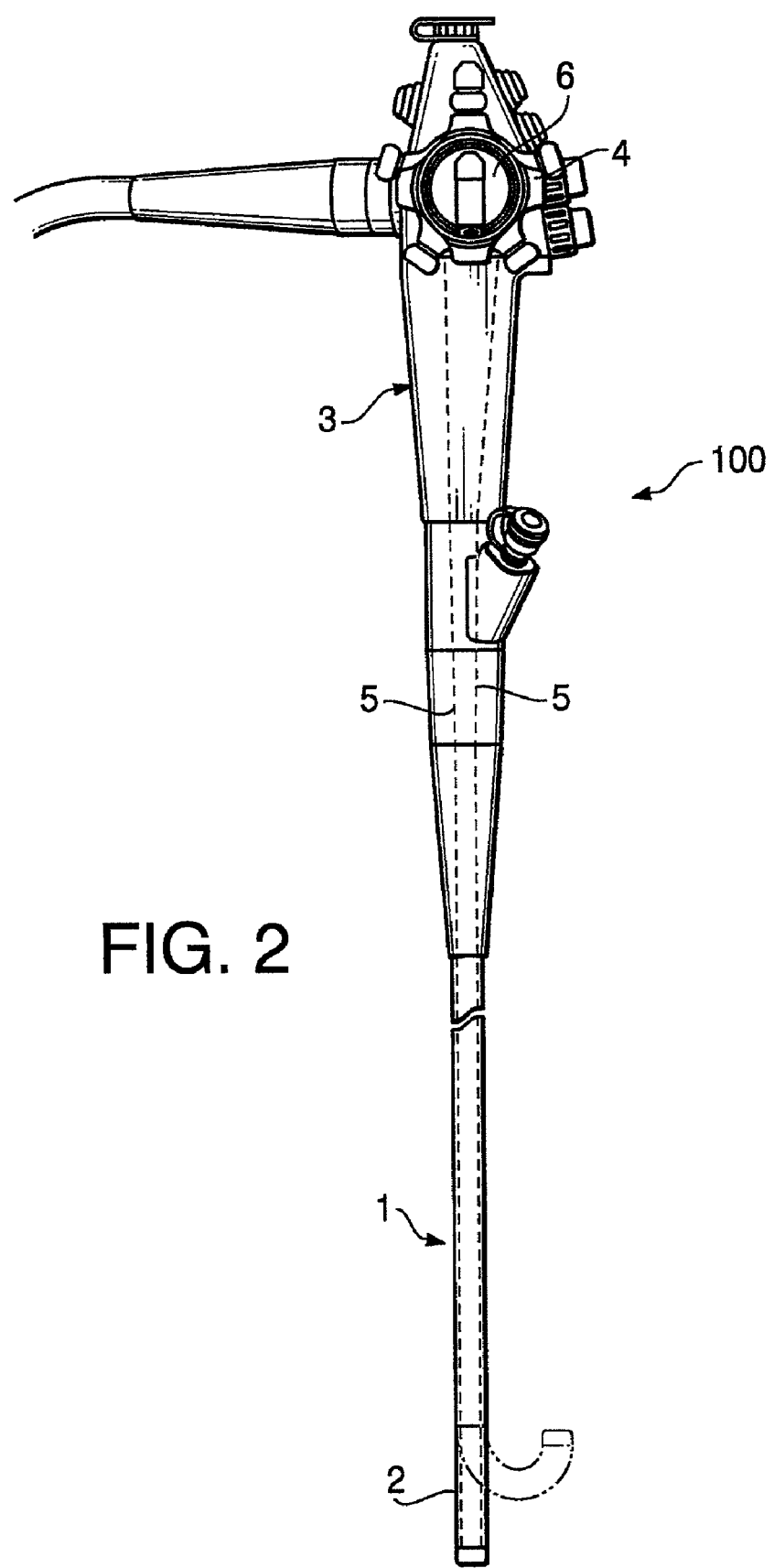
FIG. 2 is a side view of an endoscope employing the rotation mechanism shown in FIG. 1.

FIG. 2 shows a side view of an endoscope 100 to which a rotation mechanism according to the invention is applicable. The endoscope 100 has a flexible insertion section 1 and a distal end portion thereof is formed to be a bendable section 2. The bendable section 2 is driven by operation an operation unit 3 connected to the proximal end of the insertion section 1.

Specifically, the operation unit 3 is provided with a bendable section operating knob 4 (hereinafter, simply referred to as a knob), which is rotatable with respect to the operation unit 3. By rotating the knob 4, one of a plurality of operating wires 5 connected to the bendable section 2 is pulled, and the bendable section 2 is bent by an amount (i.e., angle) corresponding to the rotated amount of the knob 4. In FIG. 2, 6 denotes a bent state retaining knob to be used to retain the bent state of the bendable section 2.

Figure 1:
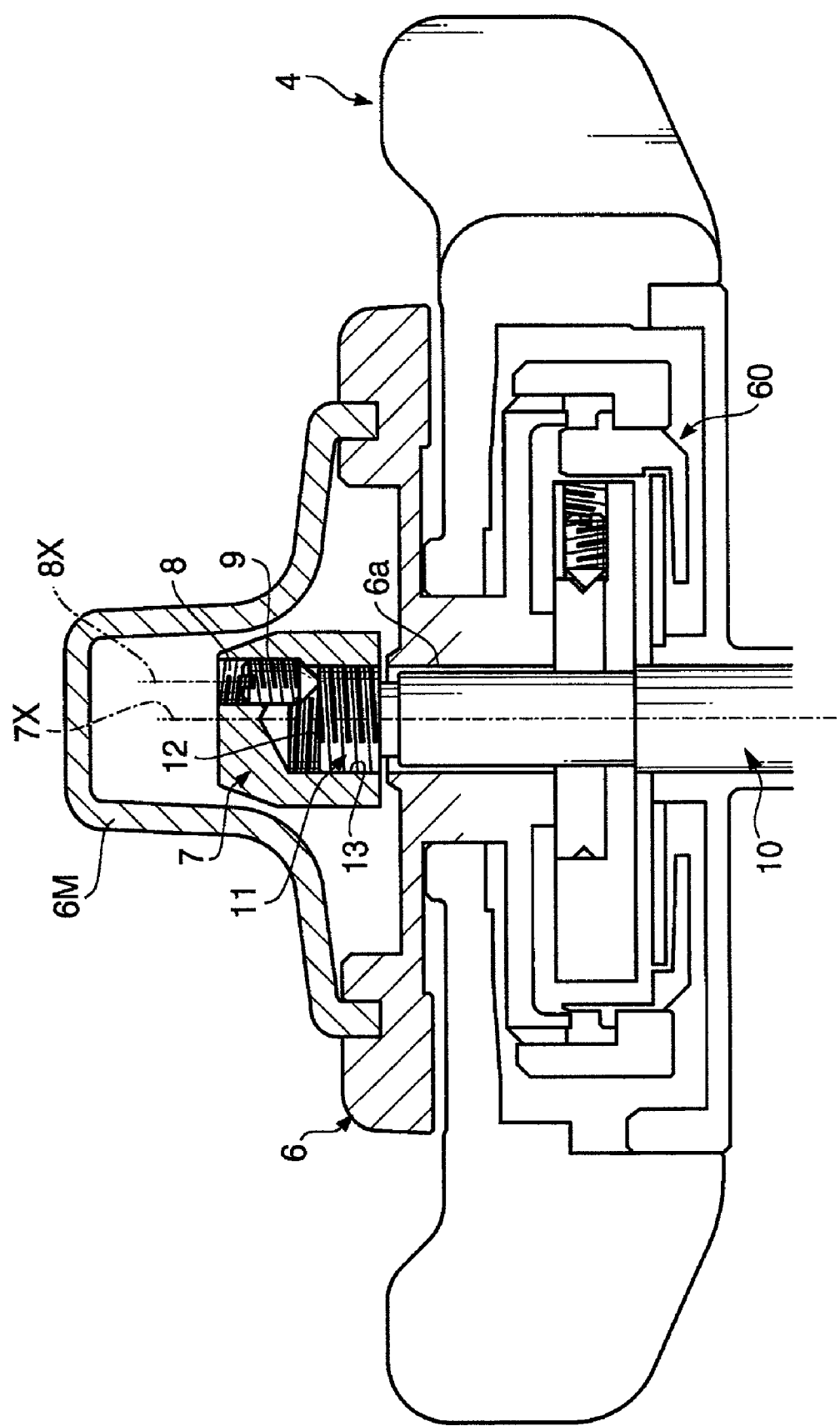
FIG. 1 is a cross-sectional side view of a rotation mechanism according to a first embodiment.

FIG. 1 is a cross-sectional side view of the rotation mechanism according to the first embodiment. In FIG. 1, 60 denotes a braking mechanism for applying frictional force for preventing the rotational movement of the knob 4 in accordance with the operation of the bent state retaining knob 6. The braking mechanism 60 is secured to a shaft member 10 which is fixedly secured onto the frame of the operation unit 3. An example of such a braking mechanism 60 is disclosed in Japanese Patent Provisional Publication No. 2007-313292.

It should be noted that the various braking mechanisms have been known, and since the present invention relates to a rotation mechanism, which is a part of the braking mechanism and may be applied to other connecting mechanism, the operation of the braking mechanism 60 will not be described for brevity.

As shown in FIG. 1, a shaft opening 6a is formed along the rotational axis of the knob 6, and the shaft member 10 is fitted in the shaft opening 6a such that the knob 6 is rotatably supported at the distal end portion of the shaft member 10.

A finger grip 6M is provided on the knob 6. The finger grip 6M is detachably attached to the knob 6 and covers the shaft opening 6a. The finger grip 6M can be detached from the knob 6 when the rotation mechanism is assembled/disassembled.

At the distal end of the shaft member 10, a thrust stopper 7 is attached to prevent the knob 6 from being removed from the shaft member 10 toward the distal end side. At the distal end portion of the shaft member 10, an outer-screw 11 is formed on the circumferential surface thereof. The thrust stopper 7 is a cap-like member having a cylindrical outer shape and a cylindrical space inside the cylindrical outer shape. The thrust stopper 7 is formed with an inner-screw 13 on the inner circumferential surface thereof. As shown in FIG. 1, the inner-screw 13 and the outer-screw 11 engage with each other when the thrust stopper 7 is attached to the shaft member 10.

The thrust stopper 7 is formed with a cylindrical through opening 8 pierced from outside to the cylindrical space thereof. The central axis 8X of the through opening 8 is parallel with but displaced from the central axis 7X of the thrust stopper 7. A screw 9 having a conical tip end is screwed in the through opening 8 as shown in FIG. 1.

By tightly fastening the screw 9, the conical tip end of the screw 9 bites into the distal end side surface 12 of the shaft member 10. Then, the rotation of the thrust stopper 7 with respect to the shaft member 10 is prevented. With the above structure, the thrust stopper 7 can be fixed at a desired position with respect to the shaft member 10.

When the rotation mechanism is assembled, firstly the knob 6 is coupled to the shaft member 10, and the thrust stopper 7 is screwed onto the distal end portion of the shaft member 10. By rotating the thrust stopper 7 with respect to the shaft member 10, the position of the thrust member 7 in the axial direction thereof is adjusted. That is, the thrust member 7 should be located at a position where the knob 6 does not have any play in the axial direction and the thrust stopper 7 does not prevent the rotational operation of the knob 6. When the position of the thrust stopper 7 is thus determined, the screw 9 is fastened tightly to prevent the thrust stopper 7 from being rotated with respect to the shaft member 10.

With the above structure, the thrust stopper 7 is fixed at an optimum position where the smooth rotation of the knob 6 without play is ensured regardless of the degree of the dimensional error of the shaft member 10.

Figure 3:
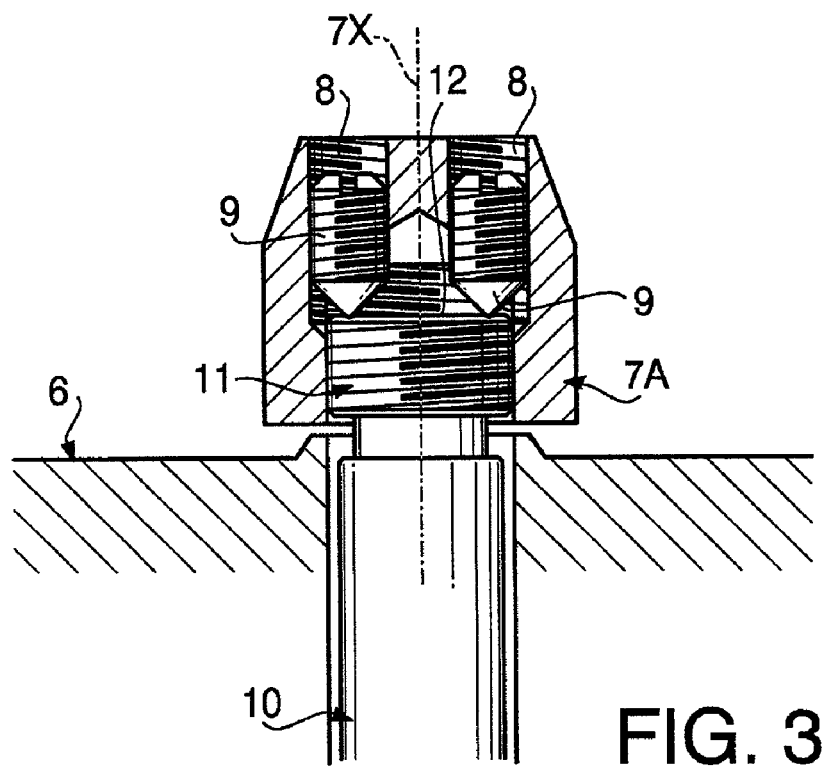
FIG. 3 is an enlarged cross-sectional side view showing a part of the rotation mechanism according to a modification of the first embodiment.

FIG. 3 is a partially enlarged cross-sectional view of the distal end portion of the shaft member 10 and the thrust stopper 7A according to a modification of the first embodiment. According to this modification, a plurality of through openings 8 are formed so that a plurality of screws 9 engage therewith, respectively. With such a structure, a fixation force of the thrust stopper 7A with respect to the shaft member 10 is enhanced. If the plurality of through openings 8 are arranged symmetrically with respect to the central axis 7X of the thrust stopper 7A, the thrust stopper 7A can be fixed to the shaft member 10 without being inclined.

Figure 4:
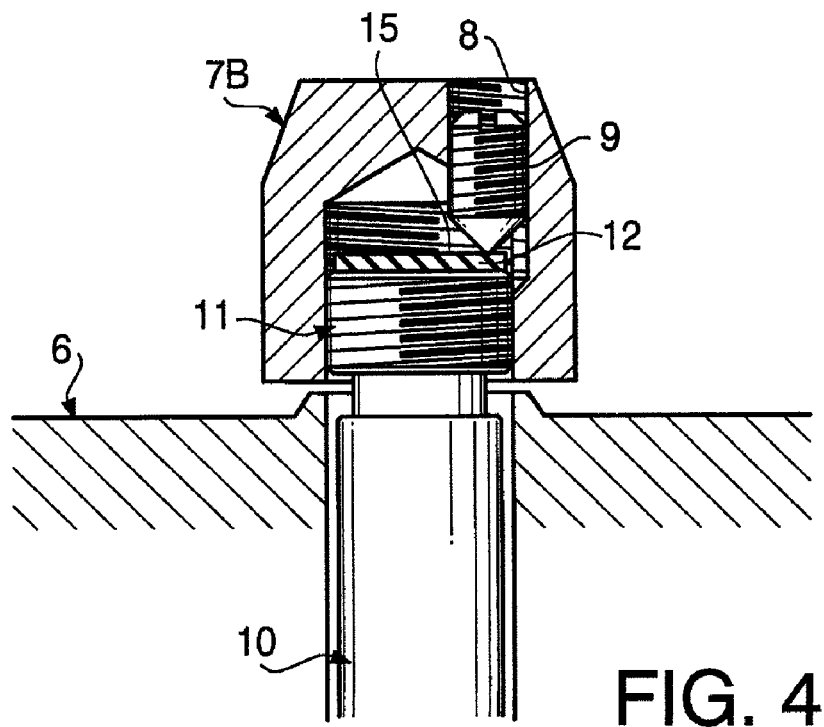
FIG. 4 is an enlarged cross-sectional side view showing a part of the rotation mechanism according to another modification of the first embodiment.

FIG. 4 is a partially enlarged cross-sectional view of the distal end portion of the shaft member 10 and the thrust stopper 7B according to another modification of the first embodiment. According to this modification, a soft member 15 is provided at the distal end surface of the shaft member 10. Specifically, as the soft member 15, a plate formed of rubber or soft plastic may be adhered on the distal end surface 12 of the shaft member 10. With this configuration, the tip end of the screw 9 bites into the soft member 15 and the fixation between the thrust stopper 7B and the shaft member 10 is consolidated.

Figure 5:
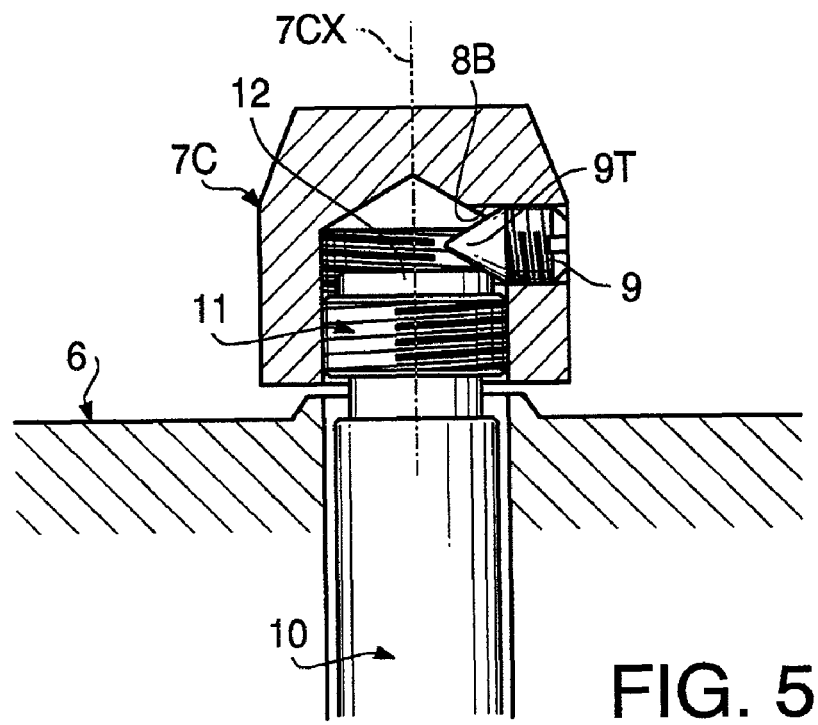
FIG. 5 is an enlarged cross-sectional side view showing a part of the rotation mechanism according to a second embodiment.

FIG. 5 is a partially enlarged cross-sectional view of the distal end portion of the shaft member 10 and the thrust stopper 7C according to a second embodiment. In the second embodiment, the through opening 8B is formed on a side (circumferential) surface of the thrust stopper 7C such that the through opening 8B extends perpendicular to an axis 7CX of the thrust stopper 7C. With this configuration, the conical tip end portion 9T of the screw 9 screwed in the through opening 8B engages with the distal end of the shaft member 10. The other portions are configured similarly to the first embodiment.

It should be noted that the tip end portion 9T should not contact or bite in the outer screw 11 since, if the tip end portion 9T contacts the outer screw 11, the outer screw 11 may deform and the thrust stopper 7C may not engage with the outer screw 11 securely. Although FIG. 5 shows that that the tip end of the screw 9 is pointed, it is not necessarily be pointed as far as the inclined surface of the tip end portion 9T contacts the distal end of the shaft member 10 and apply a sufficient force.

Figure 6:
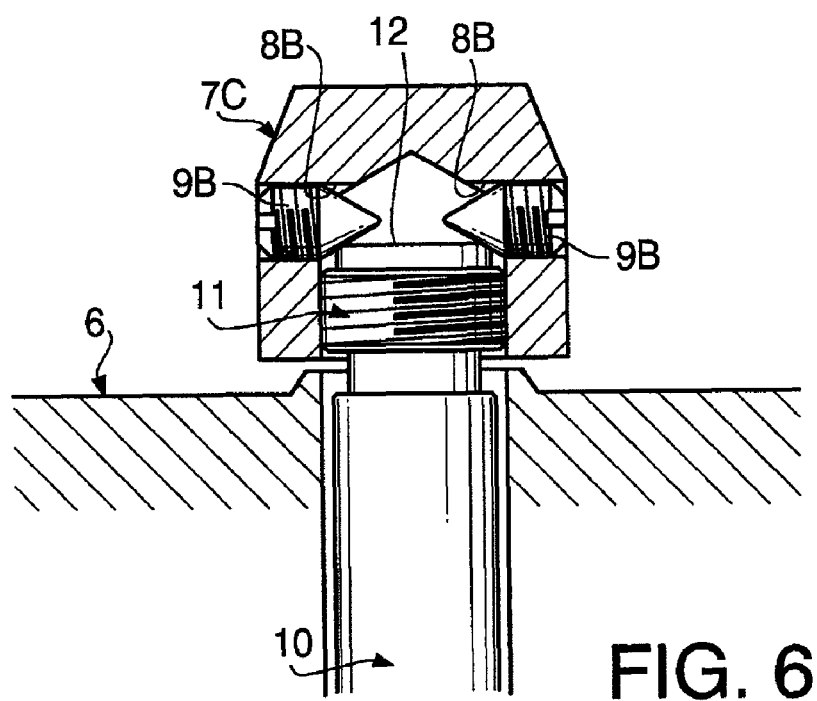
FIG. 6 is an enlarged cross-sectional side view showing a part of the rotation mechanism according to a modification of the second embodiment.

FIG. 6 is a modification of the second embodiment, which has a structure similar to the second embodiment shown in FIG. 5 except that a plurality of through openings 8B and corresponding screws 9B are used.

The present disclosure relates to the subject matter contained in Japanese Patent Application No. 2007-164779, filed on Jun. 22, 2007, which is expressly incorporated herein by reference in its entirety.

What is claimed is:

1. A connection mechanism, comprising:
a shaft member;
a rotatable member formed with a connection hole in which the shaft member is rotatably fitted at a distal end portion of the shaft member;
a thrust stopper arranged at the distal end of the shaft member to prevent the rotatable member from being removed from the shaft member,
wherein the shaft member has an outer-screw at the distal end portion thereof, the thrust stopper having an inner-screw opening extending along an axial direction of the thrust stopper, the outer-screw of the distal end portion of the shaft member engaging with the inner-screw opening, and
wherein the thrust stopper has a through opening formed with an inner-screw; and
a fixing screw configured to engage with the inner-screw of the through opening, the fixing screw inserted in the through opening and engaged with the inner-screw engaging with the distal end portion of shaft member to secure fixation between the thrust stopper and the shaft member.

2. The connection mechanism according to claim 1, wherein a tip end portion of the fixing screw is formed to have a conical shape having a pointed end, the through opening extending in a direction of a central axis of the thrust stopper displaced from the central axis of the thrust stopper, the conical tip end portion engaging with the distal end portion of the shaft member.

3. The connection mechanism according to claim 2, wherein the distal end portion of the shaft member is provided with a soft material portion.

4. The connection mechanism according to claim 1, wherein a tip end portion of the fixing screw is formed to have a conical shape, the through opening extending in a direction perpendicular with a central axis of the thrust stopper, a surface of the conical tip end portion of the fixing screw engaging with the distal end portion of the shaft member.

5. The connection mechanism according to claim 1, wherein the through opening is formed to be displaced from a central axis of the thrust stopper.

* * * * *